United States Patent [19]

Weuthen et al.

[11] Patent Number: 5,773,595
[45] Date of Patent: Jun. 30, 1998

[54] CATIONIC SUGAR SURFACTANTS

[75] Inventors: Manfred Weuthen, Solingen; Joerg Kahre, Monheim; Hermann Hensen, Haan; Holger Tesmann, Juechen, all of Germany

[73] Assignee: Henkel Kommanditgesellschaft auf Aktien, Duesseldorf, Germany

[21] Appl. No.: 722,086

[22] PCT Filed: Apr. 11, 1995

[86] PCT No.: PCT/EP95/01318

§ 371 Date: Oct. 18, 1996

§ 102(e) Date: Oct. 18, 1996

[87] PCT Pub. No.: WO95/29183

PCT Pub. Date: Nov. 2, 1995

[30] Foreign Application Priority Data

Apr. 20, 1994 [DE] Germany .................. 44 13 686.2

[51] Int. Cl.⁶ .................. C07H 15/02; C07H 1/00
[52] U.S. Cl. .................. 536/17.9; 536/4.1; 536/123.1; 536/124; 252/174.17
[58] Field of Search .................. 536/4.1, 123.1, 536/124, 17.9; 252/174.17

[56] References Cited

U.S. PATENT DOCUMENTS

| | | | |
|---|---|---|---|
| 3,931,148 | 1/1976 | Langdon | 260/210 R |
| 4,719,272 | 1/1988 | Tsai et al. | 526/238.2 |
| 5,227,481 | 7/1993 | Tsai et al. | 536/18.7 |
| 5,374,716 | 12/1994 | Biermann et al. | 536/18.6 |

FOREIGN PATENT DOCUMENTS

| | | |
|---|---|---|
| 301 298 | 2/1989 | European Pat. Off. . |
| 406 837 | 1/1991 | European Pat. Off. . |
| 432 646 | 6/1991 | European Pat. Off. . |
| 28 42 217 | 4/1980 | Germany . |
| 4-225995 | 8/1992 | Japan . |
| 4-325595 | 11/1992 | Japan . |
| WO 86/02076 | 4/1986 | WIPO . |
| WO 90/03977 | 4/1990 | WIPO . |
| WO 90/15809 | 12/1990 | WIPO . |
| WO 92/06984 | 4/1992 | WIPO . |

OTHER PUBLICATIONS

Chemical Abstracts, vol. 118, No. 9, issued 01 Mar. 1993, Yamamuro et al, "Preparation of nitrogen–containing glycosides as surfactants", p. 880, col. 1, abstract No. 81322m, Jpn. Kokai Tokkyo Koho JP 04,225,995.

C.R. CESIO World Surfactant Congress, Paris, vol. II (1984), p. 76.

Tens. Deterg. 25, 1988, p. 134.

C.R. CED Congress, Barcelona, 1992, p. 167.

Tens. Surf. Deterg. 30, 1993, pp. 186, 394.

Cosm. Toil. 106, 1991, p. 59.

Tens. Surf. Det. 26, 1989, pp. 318–324.

Surfactants in Consumer Products, Springer, Verlag, Berlin, 1987, pp. 54–124.

Kayalysatoren, Tenside und Mineralöladditive, Thieme Verlag, Stuttgart, 1978, pp. 123–217.

"Kosmetische Färbemittel" of the Farbstoffkommission der Deutschen Forschungsgemeinschaft, Verlag Chemie, Weinheim, 1984, pp. 81–106.

Primary Examiner—John Kight
Assistant Examiner—Everett White
Attorney, Agent, or Firm—Wayne C. Jaeschke; John E. Drach; Steven J. Trzaska

[57] ABSTRACT

A cationic sugar surfactant made by a process involving: (a) reacting an alkyl or alkenyl oligoglycoside of the formula (I):

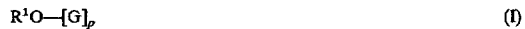

$$R^1O-[G]_p \qquad (I)$$

wherein $R^1$ is an alkyl or an alkenyl radical having from 4 to 22 carbon atoms, G is sugar unit having 5 or 6 carbon atoms and p is a number from 1 to 10, with either a chloroacetic acid, chloroacetic anhydride or chloroacetic acid methyl ester; and (b) reacting the product from step (a) with a tertiary amine of the formula (II):

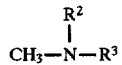
(II)
wherein each of $R^2$ and $R^3$ is an alkyl or alkenyl radical having from 1 to 22 carbon atoms.
4 Claims, No Drawings

CATIONIC SUGAR SURFACTANTS

BACKGROUND OF THE INVENTION

This invention relates to cationic sugar surfactants obtainable by reaction of alkyl and/or alkenyl oligoglucosides with quaternized halogen compounds or quaternized epoxide compounds or by reaction of the glucosides with halogen compounds and amines, to processes for the production of the cationic surfactants, to surface-active formulations containing the cationic sugar surfactants mentioned and to their use for the production of surface-active formulations.

STATEMENT OF RELATED ART

Depending on their substitution pattern, cationic surfactants of the tetraalkyl ammonium salt type are important constituents of such different products as fabric softeners, hair-care formulations, antistatic agents and sanitary cleaners.

Unfortunately, a major disadvantage of these products is that they cannot readily be processed to form stable, high-solids dispersions of low viscosity [C. R. CESIO World Surfactant Congress, Paris, Vol. II, 76 (1984)]. Accordingly, the use of typical tetraalkyl ammonium salts, such as dimethyl distearyl ammonium chloride for example, involves high costs for the packaging, storage and transport of the dilute aqueous formulations. Accordingly, there is an urgent need to remedy this situation.

Another disadvantage of cationic surfactants is that their biological degradability is questionable. It is normally assumed by experts that cationic surfactants are only degraded to a minor extent by microorganisms in a sewage treatment plant and are largely precipitated through salt formation with anionic surfactants [cf. through salt formation with anionic surfactants [cf. Tens. Deterg. 25, 134 (1988)]. In this respect, too, there is a need to develop cationic surfactants with improved ecological compatibility.

There has been no shortage of attempts in the past to provide new cationic surfactants which would represent improvements over the prior art in one respect or the other. For example, there are the so-called "esterquats"—cationic surfactants based on aminoalcohols and fatty acids [cf. O Ponsati in C. R. CED Congress, Barcelona, 1992, page 167, R. Puchta in Tens. Surf. Deterg., 30, 186 (1993) and M. Brock in Tens. Surf, Deterg. 30, 394 (1993).

Cationic sugar surfactants are also known from the prior art. Thus, according to U.S. Pat. No. 3,931,148 (BASF), glucose or starch is reacted with 0.5 to 1.2 moles of 3-chloropropane-1,2-diol in the presence of sulfuric acid, the hydrochloric acid released is neutralized and the glucoside is subsequently condensed with an amine. However, the performance properties of these products were unsatisfactory.

U.S. Pat. No. 4,719,272 (National Starch) describes cationic surfactants which are produced by reaction of glycidyl, halohydrin or haloalkyl glycosides with unsaturated amines or amidoamines, such as N,N-dimethylaminopropyl methacrylamide for example.

The subject of WO 90/15809 (Henkel Corp.) is the acetalization of cationic starch. EP-A1 0 432 646 (Union Carbide) and a corresponding article by S. Polovsky in Cosm. Toil. 106, 59 (1991) describe alkyleneoxide-containing QUATS based on alkyl polyglucosides and their use in cleaning products.

Finally, a synoptic article by T. Bocker and J. Thiem entitled "Synthese und Eigenschaften von Kohlenhydrattensiden (Synthesis and Properties of Carbohydrate Surfactants)" in Tens. Surf. Dot. 26, 324 (1989) reports on the multistage reaction of dodecyl-β-D-glucopyranoside with secondary amines.

These known products are also attended by the disadvantage that they do not meet performance requirements and/or can only be obtained with considerable effort.

Accordingly, the problem addressed by the present invention was to provide new biologically degradable quaternary ammonium compounds based on alkyl glycosides which would be distinguished by advantageous performance properties, could be used in a number of different formulations and could be produced in high yields with comparatively little effort.

DESCRIPTION OF THE INVENTION

The present invention relates to cationic sugar surfactants corresponding to formula (I):

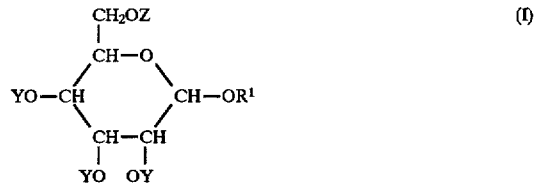

in which $R^1$ represents an alkyl and/or alkenyl radical containing 4 to 22 carbon atoms, Y is hydrogen or has the same meaning as Z and Z is a group corresponding to formula (II):

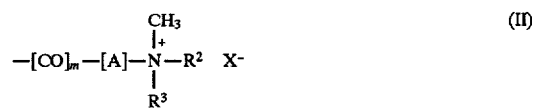

in which $R^2$ and $R^3$ independently of one another represent hydrogen, alkyl and/or alkenyl radicals containing 1 to 22 carbon atoms, A represents optionally hydroxysubstituted alkylene groups containing 1 to 10 carbon atoms, m=0 or 1 and X is halogen, alkylsulfate or alkylphosphate.

It has surprisingly been found that the cationic sugar surfactants according to the invention show excellent detergent properties and improved biological degradability. For example, the invention includes the observation that stable dispersions of high solids content and satisfactorily low viscosity can be obtained with the new cationic surfactants.

Production processes

The introduction of a quaternary ammonium group into the parent compound of the alkyl and/or alkenyl oligoglycosides known per se may be achieved in various ways, namely:

1) by reaction of a glycoside with a halogenated quaternary ammonium compound using Williamson's ether synthesis;
2) by reaction of a glycoside with a quaternized epoxide with opening of the oxirane ring;
3) by reaction of a glycoside with a dihalogen compound to form a glycoside alkyl halide ether and further reaction with a tertiary amine;
4) by reaction of a glycoside with a dihalogen compound to form a glycoside alkyl halide ether, further reaction with ammonia, a primary or secondary amine and, finally, quaternization;
5) by reaction of a glycoside with a halocarboxylic acid, a halocarboxylic acid halide, a halocarboxylic anhydride or halocarboxylic acid ester to form a glycoside alkyl halide ester and further reaction with a tertiary amine.

Alkyl and/or alkenyl oliaoglycosides

Alkyl and alkenyl oligoglycosides, which may be used as starting materials in the process according to the invention, are known nonionic surfactants which may be obtained by the relevant methods of preparative organic chemistry and which correspond to formula (II):

$$R^1O-[G]_p \qquad (II)$$

in which $R^1$ is an alkyl and/or alkenyl radical containing 4 to 22 carbon atoms, G is a sugar unit containing 5 or 6 carbon atoms and p is a number of 1 to 10. BP-A1-0 301 298 and WO 90/03977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The following observations concentrate on, but are by no means limited to, these preferred starting materials. In the interests of further simplification, the production processes are described with reference to the monoglucosides although the presence of oligoglucosides is presupposed.

The index p in general formula (II) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxo synthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil fatty alcohol having a DP of 1 to 3 are preferred.

In one particular embodiment of the invention, the alkyl and/or alkenyl oligoglycosides may also be used in the form of technical mixtures with the corresponding fatty alcohols which are formed as intermediate stages in their synthesis on an industrial scale.

Process 1:

The present invention also relates to a process for the production of cationic sugar surfactants in which alkyl and/or alkenyl oligoglucosides corresponding to formula (IV):

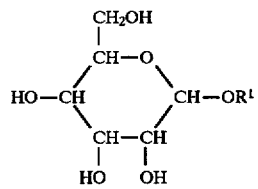

$$(IV)$$

in which $R^1$ is an alkyl and/or alkenyl radical containing 4 to 22 carbon atoms, are reacted with a halogen compound corresponding to formula (V):

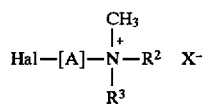

$$(V)$$

in which $R^2$ and $R^3$ independently of one another represent hydrogen, alkyl and/or alkenyl radicals containing 1 to 22 carbon atoms, A represents optionally hydroxysubstituted alkylene groups containing 1 to 10 carbon atoms, Hal represents chlorine or bromine and X represents halogen, alkylsulfate or alkylphosphate.

Typical examples of suitable halogen compounds are 3-chloro- and 3-bromo-2-hydroxypropyl trimethylammonium chloride which are marketed by Degussa AG under the name of "QUAB®". The reaction between glucoside and halogen compound takes place in the presence of strong bases, such as for example sodium hydroxide, potassium hydroxide, sodium methylate or potassium tert.butylate which may be used both in solid form and in the form of a concentrated aqueous solution. The reaction takes place typically at relatively moderate temperatures of 30° to 50° C. The reactants glucoside and halogen compound are typically used in substantially equimolar quantities, a pH value of 8 to 11 being established with the base.

Process 2:

The present invention also relates to a process for the production of cationic sugar surfactants, in which alkyl and/or alkenyl oligoglucosides corresponding to formula (IV):

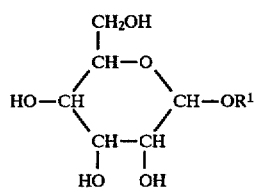

$$(IV)$$

in which $R^1$ is an alkyl and/or alkenyl radical containing 4 to 22 carbon atoms, are reacted with an epoxide compound corresponding to formula (VI):

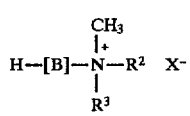

$$(VI)$$

in which $R^2$ and $R^3$ independently of one another represent hydrogen, alkyl and/or alkenyl radicals containing 1 to 22 carbon atoms, B represents alkylene groups containing 1 to 10 carbon atoms and an epoxide function and X represents halogen, alkylsulfate or alkylphosphate.

Typical examples of suitable epoxide compounds are 2,3-epoxypropyl and 2,3-epoxybutyl trimethylammonium chloride which are also marketed by Degussa AG under the name of "QUAB®". The reaction between the two reactants takes place in the form of a nucleophilic attack on the epoxide by the primary hydroxyl group of the glucoside and leads to ring opening. The reaction is preferably carried out in the presence of bases, such as sodium methylate for example, at temperatures in the range from 50° to 90° C.

Process 3:

The present invention also relates to a process for the production of cationic sugar surfactants, in which alkyl and/or alkenyl oligoglucosides corresponding to formula (IV):

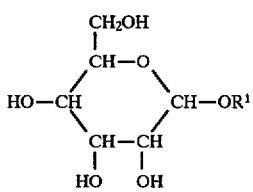

in which $R^1$ is an alkyl and/or alkenyl radical containing 4 to 22 carbon atoms, a) are reacted with an aliphatic, aromatic or araliphatic hydrocarbon containing 1 to 12 carbon atoms and 2 halogen atoms and b) the resulting ether is subsequently condensed with a tertiary amine corresponding to formula (VII):

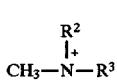

in which $R^2$ and $R^3$ independently of one another represent alkyl and/or alkenyl radicals containing 1 to 22 carbon atoms.

In this two-stage process, a substantially selective reaction between the primary hydroxyl group of the glucoside and a halide of the dihalogen compound takes place in the first stage. Typical examples of suitable dihalogen compounds are 1,4-dichlorobutane, 1,4-dibromobutane, 1,6-dichlorohexane or 1,8-dichlorooctane. To increase the yield of glucoside monoalkyl halide ethers, mixed dihalogen compounds, such as 1-bromo-2-chloroethane for example, may also be used. It is also of advantage to use tosylate as a leaving group. The degree of substitution is determined by the ratio of glucoside to dihalogen compound which is preferably 2:1 to 1:2. The etherification reaction again takes place in the presence of strong bases in the same way as for process 1 and under the same process conditions.

The glucoside alkyl halide ether is then reacted with a tertiary amine in the second stage. The tertiary amine may be selected, for example, from trimethylamine, diethyl methylamine, decyl dimethylamine, dodecyl dimethylamine, hexadecyl dimethylamine and octadecyl dimethylamine. The ether and amine are typically used in a molar ratio of approximately 0.9:1 to 1:1.2 and the condensation is carried out at temperatures in the range from 30° to 70° C. Since the viscosity can increase considerably, it is advisable to dilute the reaction mixture in portions with water.

Process 4:

The present invention also relates to a process for the production of cationic sugar surfactants, in which alkyl and/or alkenyl oligoglucosides corresponding to formula (IV):

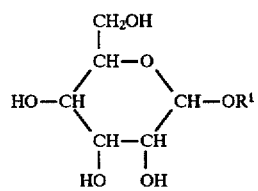

in which $R^1$ is an alkyl and/or alkenyl radical containing 4 to 22 carbon atoms, a) are reacted with an aliphatic, aromatic or araliphatic hydrocarbon containing 1 to 12 carbon atoms and 2 halogen atoms, b) the resulting ether is subsequently condensed with ammonia, a primary or secondary amine corresponding to formula (VIII):

in which $R^2$ represents hydrogen or an alkyl and/or alkenyl radical containing 1 to 22 carbon atoms and $R^3$ is an alkyl and/or alkenyl radical containing 1 to 22 carbon atoms, and c) the amine compound is quaternized in known manner with methyl halides or dimethyl sulfate.

The difference between process 4 and process 3 is that ammonia, primary or secondary amines may be used instead of the tertiary amines. Typical examples are dimethylamine, diethylamine, hexadecylamine or octadecylamine. In this case, the tertiary amine formed in the condensation step has to be alkylated in known manner in a final step, for example with dimethyl sulfate or methyl chloride, to obtain the required quaternary ammonium group.

Process 5:

The present invention also relates to a process for the production of cationic sugar surfactants in which alkyl and/or alkenyl oligoglucosides corresponding to formula (IV):

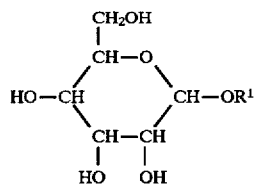

in which $R^1$ is an alkyl and/or alkenyl radical containing 4 to 22 carbon atoms, a) are reacted with a halocarboxylic acid, a halocarboxylic acid halide, a halocarboxylic anhydride or a halocarboxylic acid ester and b) the resulting ester is subsequently condensed with a tertiary amine corresponding to formula (VII):

in which $R^2$ and $R^3$ independently of one another represent alkyl and/or alkenyl radicals containing 1 to 22 carbon atoms.

The difference between process 5 and process 3 is that, instead of the ether, an ester is formed as the intermediate stage and is subsequently condensed with a tertiary amine. To prepare the glucoside alkyl halide esters, the glucosides may be reacted with halogenated acids, halogenated acid chlorides, halogenated anhydrides or halogenated esters. Typical examples are chloroacetic acid, chloroacetic anhydride or chloroacetic acid methyl ester. The ratio of glucoside to halogen compound is typically of the order of 1:0.9 to 1:1.2. The reaction is carried out in the absence of a catalyst at temperatures in the range from 50° to 120° C. Accordingly, a base is required as catalyst for the subsequent condensation with the amine. Tertiary amines are preferably used in this variant of the process because primary and secondary amines show a tendency towards recleavage of the esters.

Detergent mixtures

The cationic sugar surfactants may be used either on their own or in combination with other anionic, nonionic, cationic and/or amphoteric or zwitterionic surfactants.

Typical examples of anionic surfactanta are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, alkyl oligoglucoside sulfates and alkyl(ether) phosphates. If the anionic surfactants contain polyglycol ether chains, they may have a conventional homolog distribution although they preferably have a narrow-range homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, alk(en)yl oligoglycosides, fatty acid N-alkyl glucamides, polyol fatty acid esters, sugar esters, sorbitan esters and polysorbates. If the nonionic surfactants contain polyglycol ether chains, they may have a conventional homolog distribution, although they preferably have a narrow-range homolog distribution.

Typical examples of cationic surfactants are quaternary ammonium compounds and esterquats, more particularly quaternized fatty acid trialkanolamine ester salts.

Typical examples of amphoteric or zvitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral oil Additives)", Thieme Verlag, Stuttgart, 1978, pages 123–217.

Commercial Applications

The cationic sugar surfactants according to the invention have excellent detergent properties, are readily soluble or dispersible in cold water and are distinguished by good ecotoxicological compatibility. The surfactants provide textiles and fibers with a pleasant soft feel and with an antistatic finish. They have a foam-stabilizing effect, improve the wet and dry combability of hair and show microbistatic activity.

Surface active formulations

Accordingly, the present invention also relates to surface-active formulations which contain these detergent mixtures and which are defined more closely in the following:

Powder-form heavy-duty detergents containing 10 to 30% by weight, based on the detergent, of cationic sugar surfactants and also typical auxiliaries and additives.

Liquid heavy-duty detergents containing 10 to 70% by weight, based on the detergent, of cationic sugar surfactants and also typical auxiliaries and additives.

Liquid light-duty detergents containing 10 to 50% by weight, based on the detergent, of cationic sugar surfactants and also typical auxiliaries and additives.

Manual dishwashing detergents containing 10 to 50% by weight, based on the detergent, of cationic sugar surfactants and also typical auxiliaries and additives.

Rinse aids containing 10 to 50% by weight, based on the rinse aid, of cationic sugar surfactants and also typical auxiliaries and additives.

Liquid cleaners and disinfectants containing 10 to 30% by weight, based on the cleaner/disinfectant, of cationic sugar surfactants and also typical auxiliaries and additives.

Hair shampoos containing 10 to 30% by weight, based on the shampoo, of cationic sugar surfactants and also typical auxiliaries and additives.

Hair rinses containing 10 to 30% by weight, based on the hair rinse, of cationic sugar surfactants and also typical auxiliaries and additives.

Foam baths containing 10 to 30% by weight, based on the foam bath, of cationic sugar surfactants and also typical auxiliaries and additives.

Flotation aids containing 10 to 30% by weight, based on the flotation aid, of cationic sugar surfactants and also typical auxiliaries and additives.

Auxiliaries and additives

Laundry detergents, dishwashing detergents, cleaning formulations and fabric softeners based on the sugar surfactants according to the invention may contain, for example, builders, salts, bleaches, bleach activators, optical brighteners, redeposition inhibitors, solubilizers and enzymes as auxiliaries and additives.

Typical builders are sodium aluminium silicates (zeolites), phosphates, phosphonates, ethylenediamine tetraacetic acid, nitrilotriacetate, citric acid and/or polycarboxylates. Suitable salts or diluents are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Skin-care formulations, such as creams, lotions and the like, generally contain oils, emulsifiers, fats and waxes, stabilizers and also superfatting agents, thickeners, biogenic agents, film formers, preservatives, dyes and fragrances in addition to the surfactants already mentioned.

Hair-care formulations, for example hair shampoos, hair lotions, foam baths and the like may contain emulsifiers, superfatting agents, thickeners, biogenic agents, film formers, preservatives, dyes and fragrances as further auxiliaries and additives in addition to the surfactants already mentioned.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{16-18}$ fatty alcohols, esters of linear $C_{10-18}$ fatty acids with branched alcohols, more especially 2-ethyl hexanol, esters of linear and/or branched fatty acids with dihydric alcohols and/or Guerbet alcohols, triglycerides based on $C_{6-10}$ fatty acids, vegetable oils, branched primary alcohols, substituted cyclohexanes, Guerbet carbonates and/or dialkyl ethers.

Suitable emulsifiers are both known w/o and o/w emulsifiers, for example hydrogenated and ethoxylated castor oil, polyglycerol fatty acid esters or polyglycerol polyricinoleates.

Typical examples of fats are glycerides while suitable waxes are inter alia beeswax, paraffin wax or microwaxes, optionally in combination with hydrophilic waxes, for example cetostearyl alcohol.

Metal salts of fatty acids, for example magnesium, aluminium and/or zinc stearate, may be used as stabilizers.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, narrow-range fatty alcohol ethoxylates or alkyl oligoglucosides and electrolytes, such as sodium chloride and ammonium chloride.

In the context of the invention, biogenic agents are, for example, plant extracts and vitamin complexes.

Typical film formers are, for example, chitosan, microcrystalline chitosan or quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, phenoxyethanol, formaldehyde solution, parabens, pentanediol or sorbic acid.

Suitable pearlescers are, for example, glycol distearic acid esters, such as ethylene glycol distearate, and also fatty acid monoglycol esters.

The dyes used may be selected from any of the substances which are permitted and suitable for cosmetic purposes, as listed for example in the publication "Kosmetische F ärbemittel" of the Parbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total percentage content of the auxiliaries and additives may be from 1 to 50% by weight and is preferably from 5 to 40% by weight while the non-aqueous component ("active substance content") may be from 20 to 80% by weight and is preferably from 30 to 70% by weight, based on the particular formulation. Formulations may be produced in known manner, i.e. for example by hot, cold, hot-hot/cold and PIT emulsification. These are purely mechanical processes which do not involve a chemical reaction.

Finally, the present invention relates to the use of the cationic sugar surfactants according to the invention for the production of surface-active formulations, such as for example laundry detergents, dishwashing detergents, cleaning formulations, fabric softeners and flotation aids and also hair-care and body-care products in which they may be present in quantities of 1 to 50% by weight and preferably 5 to 30% by weight, based on the particular formulation.

EXAMPLES

I. Synthesis Examples

Example 1

Reaction of dodecyl glucoside with 3-chloro-2-hydrozypropyl trizethylammonium chloride (surfactant A)

380 g (1 mole) of dodecyl glucoside (DP=1.3) were dissolved in 380 g of water and 315 g (1 mole) of 3-chloro-2-hydroxypropyl trimethylammonium chloride (QUAB® 188, a product of Degussa AG, Hanau, FRG) were added to the resulting solution at 20° C. The reaction mixture was heated to 40° C. and aqueous 50% by weight sodium hydroxide solution was then added until a constant pH value of 9.5 was established. The mixture was then stirred for 46 hours at 40° C. and subsequently heated for 2 hours to 90° C. 1150 g of cationic sugar surfactant in the form of a 54% by weight light-colored product paste were obtained. The percentage content of unreacted glucoside was 8% by weight, corresponding to a conversion of 75% of the theoretical.

Example 2

Reaction of $C_{16/18}$ alkyl glucoside with 2,3-epozypropyl trimethylammonium chloride (surfactant B)

1450 g (1 mole) of $C_{16/18}$ alkyl glucoside (31% by weight solution in $C_{16/18}$ fatty alcohol, Emulgade® PL1618, a product of Henkel KGaA, Düsseldorf, FRG) were heated to 70° C. and 4 g of the sodium methylate (30% by weight in methanol) were then added. To remove the methanol, a vacuum of 8 to 10 mbar was applied. 216 g (1 mole) of 2,3-epoxypropyl trimethylammonium chloride (70% by weight in water, QUAB® 151, a product of Degussa AG, Hanau, FRG) were then added dropwise to the mixture at normal pressure, followed by stirring for another 48 h at 70° C. 1667 g of cationic sugar surfactant in the form of a light colored wax-like mass containing 7% by weight of unreacted glucoside were obtained. The conversion, based on the glucoside, amounted to 73% of the theoretical; based on the epoxide, it was quantitative.

Example 3

Reaction of hexadecyl glucoside with 1,4-dichlorobutane and hexadecyl dimethylamine (surfactant C)

a) 440 g (1 mole) of hexadecyl glucoside (DP=1.4) were dissolved in 635 g (5 moles) of 1,4-dichlorobutane at 80° C. and 56 g (1 mole) of potassium hydroxide pellets were added to the resulting solution. The reaction mixture was stirred for 7 hours at 100° C., filtered, the filtrate was poured onto 100 ml of water and, after shaking, the organic phase was separated off and the excess 1,4-dichlorobutane was distilled off under a reduced pressure of 1 mbar. 528 g of a chlorinated ether with an average degree of substitution of 0.98 and a residual glucoside content of 21% by weight were obtained.

b) The chlorinated ether from 3a) was dissolved in 350 g of water and 300 g (1.1 moles) of hexadecyl dimethylamine were added to the resulting solution.

The emulsion was stirred for 48 h at 50° C. and diluted with 805 g of water to reverse the increase in viscosity. The resulting paste was then adjusted to pH 12 with 50% by weight aqueous sodium hydroxide solution and was purified by stripping with steam in a thin layer evaporator under slightly reduced pressure at a temperature of 70° C.

1900 g of a yellow-colored paste with a solids content of 39% by weight were obtained.

Example 4

Reaction of hexadecyl glucoside with chloroacetic anhydride and hexadecyl dimethylamine (surfactant D)

a) 440 g (1 mole) of hexadecyl glucoside (DP=1.4) were dissolved in 205 g (1.2 mole) of chloroacetic anhydride. The mixture was then heated to 110° C. and chloroacetic acid was distilled off through a column under a reduced pressure of 50 mbar. 80 g of distillate, of which 20% by weight consisted of chloroacetic anhydride, were obtained over a period of 2 hours. The vacuum was then reduced to around 1 mbar, the residual chloroacetic acid or the anhydride distilling off. 529 g of a chlorinated ether with an average degree of substitution of 0.95 and a residual glucoside content of 14% by weight were obtained.

b) The chlorinated ether from 4a) was dissolved in 285 g of water and the resulting solution was adjusted to pH 8.5 by the addition at 20° C. of a 10% by weight aqueous sodium hydroxide solution. 242 g (0.9 mole) of hexadecyl dimethylamine were added to the paste obtained. The emulsion was stirred for 48 hours at 50° C. and diluted with 472 g of water to reverse the increase in viscosity. The resulting paste was then purified by stripping with steam in a thin layer evaporator under slightly reduced pressure at a temperature of 70° C.

1890 g of a yellow-colored paste with a solids content of 42% by weight were obtained.

II. Formulation Examples

1. Liquid detergent with fabric-softening properties:
Texapon® NSO . . . 44% by weight
Dehydol® LT 7 . . . 15% by weight
Plantaren® 2000 . . . 15% by weight
Cationic sugar surfactant A . . . 8% by weight
Cumene sulfonate Na salt . . . 4% by weight
Water . . . ad 100

The detergent mixture has excellent washing and fabric-softening properties and, in addition, provides the treated textiles with an antistatic finish.

2. sanitary cleaner
Cationic sugar surfactant B . . . 10% by weight
Plantaren® 225 . . . 7% by weight
Water . . . ad 100

The detergent mixture has excellent cleaning properties coupled with a disinfecting effect.

3. Heavy-duty detergent with fabric-softening properties
Sodium tripolyphosphate . . . 45% by weight
Sodium carbonate . . . 20% by weight
Sodium silicate . . . 15% by weight
Plantaren® 2000 . . . 15% by weight
Cationic sugar surfactant C . . . 4.5% by weight
Protease . . . 0.5% by weight The powder mixture has very good washing and cleaning properties. In contrast to typical detergents containing cationic surfactants, no redeposition of soil on the fibers is observed.

4. Light-duty detergent with fabric-softening properties
Plantaren® 2000 . . . 16% by weight
Cationic sugar surfactant D . . . 4% by weight
Water . . . ad 100

The detergent mixture combines the properties of a light-duty detergent with those of a fabric softener.

5. Hair rinse (I)
Emulgade® PL 1618 . . . 4.0% by weight
Nutrilan® Keratin W . . . 2.3% by weight
Plantaren® 1200 . . . 2.0% by weight
Cationic sugar surfactant B . . . 1.0% by weight
Lameform® TGI . . . 1.0% by weight
Cetiol® V . . . 1.0% by weight
Cutina® MD . . . 0.5% by weight
Water, preservative ad 100

6. Hair rinse (II)
Lanette® O . . . 2.5% by weight
Cationic sugar surfactant C . . . 1.0% by weight
Cetiol® OE . . . 1.0% by weight
Eumulgin® B2 . . . 0.8% by weight
Cutina® MD . . . 0.5% by weight
Water, preservative . . . ad 100

7. Hair rinse (III)
Lanette® O . . . 2.5% by weight
Cationic sugar surfactant B . . . 1.0% by weight
Eutanol® G . . . 1.0% by weight
Eumulgin® B2 . . . 0.8% by weight
Cutina® MD . . . 0.5% by weight
Water, preservative . . . ad 100

8. Hair rinse (IV)
Lanette® O . . . 2.5% by weight
Nutrilan® I-50 . . . 2.0% by weight
Cationic sugar surfactant A . . . 1.0% by weight
Lameform® TGI . . . 1.0% by weight
Cetiol® V . . . 1.0% by weight
Eumulgin® B2 . . . 0.8% by weight
Cutina® MD . . . 0.5% by weight
Water, preservative . . . ad 100

9. Leave-on hair rinse
Sepigel® 305 . . . 3.0% by weight
Nutrilan® I-50 . . . 2.0% by weight
Cationic sugar surfactant D . . . 0.8% by weight
Plantaren® 1200 . . . 0.5% by weight
Cetiol® J 600 . . . 0.5% by weight
Copherol® 1250 . . . 0.2% by weight
Ethanol . . . 10.0% by weight
Glycerol, 86% by weight . . . 5.0% by weight
Water, preservative . . . ad 100

10. Hair conditioner (I)
Lanette® O . . . 3.0% by weight
Generol® 122 . . . 1.0% by weight
Cationic sugar surfactant A . . . 1.0% by weight
Eumulgin® B2 . . . 0.8% by weight
Cutina® MD . . . 0.5% by weight
Water . . . ad 100

11. Hair condition (II)
Lanette® O . . . 2.5% by weight
Cationic sugar surfactant D . . . 1.5% by weight
Eumulgin® B2 . . . 1.0% by weight
Generol® 122 . . . 1.0% by weight
Eutanol® G . . . 1.0% by weight
Cutina® MD . . . 0.5% by weight 12. Shower bath (I)
Texapon® K 14 S spez. . . . 38.0% by weight
Plantaren® 2000 . . . 7.0% by weight
Lamesoft® LMG . . . 3.0% by weight
Arlypon® F . . . 3.0% by weight
Cationic sugar surfactant C . . . 0.5% by weight
Water, preservative . . . ad 100

13. shower bath (II)
Texapon® NSO . . . 38.0% by weight
Plantaren® 2000 . . . 7.0% by weight
Euperlan® PK 3000-AM . . . 3.0% by weight
Arlypon® F . . . 3.0% by weight
Lamesoft® LMG . . . 2.0% by weight
Cationic sugar surfactant B . . . 0.5% by weight
NaCl . . . 1.5% by weight
Water, preservative . . . ad 100

14. shower gel
Texapon® NSO . . . 25.0% by weight
Texapon® SB3 . . . 10.0% by weight
Dehyton® K . . . 10.0% by weight
Plantaren® 2000 . . . 6.0% by weight
Euperlan® PK 3000-AM . . . 5.0% by weight
Lamesoft® LMG . . . 4.0% by weight
Antil® 141 L . . . 1.5% by weight
Cetiol® HE . . . 1.0% by weight
Arlypon® F . . . 1.0% by weight
Cationic sugar surfactant A . . . 0.5% by weight
Water, preservative . . . ad 100

15. Wash lotion
Plantaren® PS10 . . . 16.0% by weight
Euperlan® PK 900 . . . 5.0% by weight
Cationic sugar surfactant D . . . 0.5% by weight NaCl ... 1.5% by weight
Water, preservative ... ad 100
  16. "Two-in-one" shower bath (I)
Texapon® NSO ... 20.0% by weight
Dehyton® K ... 20.0% by weight
Plantaren® 2000 ... 5.0% by weight
Nutrilan® I-50 ... 1.0% by weight
Cationic sugar surfactant C ... 1.0% by weight
Euperlan® PH 3000-AM ... 5.0% by weight
Lytron® 631 ... 2.0% by weight
Arlypon® F ... 0.6% by weight
Water, Preservative ... ad 100
  17. "Two-in-one" shower bath (II)
Texapon® NSO ... 20.0% by weight
Dehyton® K ... 20.0% by weight
Plantaren® 2000 ... 5.0% by weight
Cationic sugar surfactant B ... 1.5% by weight
Euperlan® PH 3000-AM ... 3.0% by weight
Cetiol® HE ... 0.2% by weight
Lytron® 631 ... 1.0% by weight
Arlypon® F ... 0.6% by weight
Glycerol, 86% by weight ... 5.0% by weight
Water, Preservative ... ad 100
  "Two-in-one" shower bath (III)
Texapon® ASV 70 spez ... 12.4% by weight
Plantaren® 1200 ... 4.0% by weight
Cationic sugar surfactant B ... 4.0% by weight
Euperlan® PH 3000-AM ... 4.0% by weight
Panthenol USP ... 1.0% by weight
Water, Preservative ... ad 100
  19. "Two-in-one" shower bath & emulsion
Plantaren® PS 10 ... 40.0% by weight
Eumulgin® B2 ... 1.0% by weight
Eutanol® G ... 3.0% by weight
Lamecreme® DGE 18 ... 4.0% by weight
Lytron® 631 ... 1.0% by weight
Cationic sugar surfactant A ... 1.0% by weight
Perfume ... 0.5% by weight
Water, preservative ... ad 100
  20. Shampoo (I)
Texapon® NSO ... 25.0% by weight
Plantaren® 2000 ... 5.0% by weight
Dehyton® K ... 8.0% by weight
Cationic sugar surfactant A ... 3.0% by weight
Arlypon® F ... 1.5% by weight
Eumulgin® L ... 1.0% by weight
Perfume ... 5.0% by weight
  21. Shampoo (II)
Texapon® N 70 ... 11.0% by weight
Texapon® SB 3 ... 7.0% by weight
Plantaren® 1200 ... 4.0% by weight
Cationic sugar surfactant C ... 1.0% by weight
Nutrilan® I-50 ... 2.0% by weight
NaCl ... 1.6% by weight
Water, preservative ... ad 100
  22. Shampoo (III)
Plantaren® PS 10 ... 16.0% by weight
Cationic sugar surfactant B ... 2.0% by weight
NaCl ... 2.0% by weight
Water, preservative ... ad 100
  23. Shampoo (IV)
Plantaren® PS 10 ... 17.0% by weight
Nutrilan® I-50 ... 2.0% by weight
Cationic sugar surfactant A ... 2.0% by weight
Glycerol, 86% by weight ... 1.0% by weight
Euperlan® PK 900 ... 3.0% by weight
NaCl ... 2.2% by weight Water, preservative ... ad 100
  24. Shampoo (V)
Texapon® N 70 ... 11.0% by weight
Plantaren® 1200 ... 6.0% by weight
Nutrilan® I-50 ... 2.0% by weight
Cationic sugar surfactant D ... 2.0% by weight
Euperlan® PK 900 ... 3.0% by weight
NaCl ... 3.0% by weight
Water, preservative ... ad 100
  25. Shampoo (V)
Texapon® ALS ... 23.0% by weight
Plantaren® 2000 ... 4.0% by weight
Dehyton® K 50 ... 7.0% by weight
Cationic sugar surfactant C ... 2.0% by weight
Lamesoft® 156 ... 5.0% by weight
Monomuls 90-L 12 ... 1.0% by weight
NaCl ... 3.0% by weight
Water, preservative ... ad 100
  26. Foam bath (I)
Plantaren® PS 10 ... 22.0% by weight
Dehyton® K ... 15.0% by weight
Cationic sugar surfactant B ... 3.0% by weight
Cetiol® HE ... 2.0% by weight
Euperlan® PK 3000-OK ... 5.0% by weight
Water, preservative ... ad 100
  27. Foam bath (II)
Texapon® NSO ... 30.0% by weight
Dehyton® K ... 10.0% by weight
Plantaren® 1200 ... 10.0% by weight
Lamesoft® LMG ... 4.0% by weight
Cationic sugar surfactant A ... 2.0% by weight
Guadin® APG ... 0.5% by weight
Water, preservative ... ad 100
  28. Foam bath (III)
Melissa oil ... 5.0% by weight
Eumulgin® L ... 15.0% by weight
Plantaren® 2000 ... 30.0% by weight
Dehyton® K ... 10.0% by weight
Cationic sugar surfactant D ... 4.0% by weight
Antil® 141 liquid ... 3.8% by weight
Arlypon® F ... 1.5% by weight
Water, preservative ... ad 100
  29. Foam bath (IV)
Plantaren® PS 10 ... 22.0% by weight
Dehyton® K ... 15.0% by weight
Cationic sugar surfactant C ... 2.0% by weight
Cetiol® HE ... 2.0% by weight
Euperlan® PK 3000-OK ... 5.0% by weight
Water, preservative ... ad 100
  30. Foam bath concentrate
Texapon® K 14 S 70 spez. ... 25.0% by weight
Plantaren® 2000 ... 20.0% by weight
Dehyton® K ... 20.0% by weight
Cationic sugar surfactant B ... 5.0% by weight
Cetiol® HE ... 5.0% by weight
Nutrilan® I-50 ... 2.0% by weight
Eumulgin® HRE 60 ... 5.0% by weight
Citric acid (50% by weight) ... 0.5% by weight
Water, preservative ... ad 100
  31. Collector for the flotation of non-sulfide ores
Dehypon® LT 104 ... 25% by weight
Cationic sugar surfactant A ... 25% by weight
Water ... ad 100

The trade names and corresponding CTFA names are shown in Table 1.

TABLE 1

Trade Names and CTFA Names

| Trade Name | | CTFA Name |
|---|---|---|
| Antil | 141 | Propylene glycol (and) PEG-55 Propylene Glycol Oleate |
| Arlypon | F | Laureth-2 |
| Cetiol | HE PEG-7 | Glyceryl Cocoate |
| | J 600 | Oleyl Erucate |
| | OE | Dicapryl Ether |
| | V | Decyl Oleate |
| Copherol | 1250 | Tocopheryl Acetate |
| Cutina | MD | Glyceryl Stearate |
| Dehydol | LT 7 | Laureth-7 |
| Dehyton | K | Cocamidopropyl Betaine |
| Emulgade | PL 1618 | Hexadecyl Polyglucose (and) Hexadecyl Alcohol |
| Euperlan | PK 900 | Triethylene Glycol Distearate (and) Sodium Laureth Sulfate |
| | PK 3000-AM | Glycol Distearate (and) Laureth-4 (and) Cocoamidopropyl Betaine |
| | PK 3000-OK | Glycol Distearate (and) Glycerin (and) Laureth-4 (and) Cocoamidopropyl Betaine |
| Eumulgin | B2 | Ceteareth-20 |
| | HRE 60 | PEG 60 Hydrogenated Castor Oil |
| | L | PPG-2-Ceteareth-9 |
| Eutanol | G | Octyldodecanol |
| Generol | 122 | Soya Sterol |
| Guadin | AGP | Hydrolyzed Wheat Protein |
| Lamecreme | DGE 18 | Polyglyceryl-2-PEG-4 Copolymer |
| Lameform | LMG | Glyceryl Laurate (and) Potassium Cocoyl Hydrolyzed Collagen |
| | TGI | Polyglyceryl-3 Diisostearate |
| Lamesoft | 156 | Hydrogenated Tallow Glycerides (and) Potassium Cocoyl Hydrol. Collagen |
| | LMG | Glyceryl Laurate (and) Potassium Cocoyl Hydrolyzed Collagen |
| Lanette | O | Cetearyl Alcohol |
| Lytron | 631 | Sodium Styrene/Acrylates Copol. |
| Monomuls | 90-L 12 | Glyceryl Laurate |
| Nutrilan | W | Hydrolyzed Keratin |
| Plantaren | 225 | Capryl Polyglucose |
| | 1200 | Lauryl Polyglucose |
| | 2000 | Decyl Polyglucose |
| | PS 10 | Sodium Laureth Sulfate (and) Lauryl Polyglucose |
| Texapon | ALS | Ammonium Laureth Sulfate |
| | ASV 70 | Sodium Laureth Sulfate (and) Sodium Laureth-8 Sulfate (and) Sodium Oleth sulfate |
| | K 14 S | Sodium Myreth Sulfate |
| | N 70 | Sodium Laureth Sulfate |
| | NSO | Sodium Laureth Sulfate |
| | SB 3 | Disodium Laurethsulfosuccinate |

What is claimed is:

1. A cationic sugar surfactant made by the process which comprises the steps of (a) reacting an alkyl or alkenyl oligoglycoside of the formula (I):

$$R^1O-[G]_p \qquad (I)$$

wherein $R^1$ is an alkyl or an alkenyl radical having from 4 to 22 carbon atoms, G is sugar unit having 5 or 6 carbon atoms and p is a number from 1 to 10 with chloroacetic acid, chloroacetic anhydride or chloroacetic acid methyl ester; (b) reacting the product from step (a) with a tertiary amine of the formula (II):

$$\begin{array}{c} R^2 \\ | \\ CH_3-N-R^3 \end{array} \qquad (II)$$

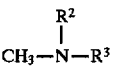

wherein each of $R^2$ and $R^3$ is an alkyl or alkenyl radical having from 1 to 22 carbon atoms.

2. A surface-active composition containing the cationic sugar surfactant of claim 1.

3. A surface active formulation selected from the group consisting of a laundry detergent, a dishwashing detergent, a fabric softener, a sanitary cleaner, a fabric softener, a flotation aid, a shampoo, a hair rinse aid, a hair conditioner, a personal cleanser comprised of from about 1% to about 50% by weight of a cationic sugar surfactant of claim 1.

4. A process for making a cationic sugar reactant made by the process which comprises the steps of: (a) reacting an alkyl or alkenyl oligoglycoside of the formula (I):

$$R^1O-[G]_p \qquad (I)$$

wherein $R^1$ is an alkyl or an alkenyl radical having from 4 to 22 carbon atoms, G is sugar unit having 5 or 6 carbon atoms and p is a number from 1 to 10 with chloroacetic acid, chloroacetic anhydride or chloroacetic acid methyl ester; (b) reacting the product from step (a) with a tertiary amine of the formula (II):

$$\begin{array}{c} R^2 \\ | \\ CH_3-N-R^3 \end{array} \qquad (II)$$

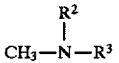

* * * * *